United States Patent [19]

Patel

[11] Patent Number: 5,354,740
[45] Date of Patent: Oct. 11, 1994

[54] DIARYL(PYRIDINIO AND ISOQUINOLINIO) BORON FUNGICIDAL AGENTS

[75] Inventor: Bomi P. Patel, Philadelphia, Pa.

[73] Assignee: American Cyanamid Company, Wayne, N.J.

[21] Appl. No.: 59,048

[22] Filed: May 7, 1993

[51] Int. Cl.$^5$ .............................................. A01N 55/08
[52] U.S. Cl. ...................................................... 514/64
[58] Field of Search ......................................... 514/64

[56] References Cited

U.S. PATENT DOCUMENTS

| | | | |
|---|---|---|---|
| 3,211,679 | 10/1965 | Updegraff | 260/19 |
| 4,983,589 | 1/1991 | Tszeng | 514/64 |
| 4,983,590 | 1/1991 | Tszeng | 514/64 |

OTHER PUBLICATIONS

H. J. Frohn, et al, Eur. J. Solid State Inorg. Chem., 29(4–5), pp. 729–738 (1992).
W. Regnt, et al, Chem. Ber., 104(3), pp. 722–733 (1971).
J. Soulie and P. Cadiot, Bull. Soc. Chim. France, (6), pp. 1981–1992 (1966).
B. M. Mikhailov and N. S. Fedotov, Zh. Obshch. Khim., 32, pp. 93–95 (1962).
E. W. Abel, et al. J. Chem. Soc., pp. 2895–2897 (1958).
B. M. Mikhailov and N. S. Fedotov, Izvest. Akad. Nauk S.S.S.R., Oldel. Khim. Nauk, pp. 1511–1513 (1956).
R. Koester, et al, Justus Liebigs Ann. chem., 724, pp. 34–55 (1969).
J. J. Eisch, et al, Heterocycles, 18 (Spec. Issue), pp. 245–250 (1982).

*Primary Examiner*—Allen J. Robinson
*Attorney, Agent, or Firm*—John W. Hogan, Jr.

[57] ABSTRACT

There are provided diaryl(pyridinio and isoquinolinio)-boron compounds having the structural formula

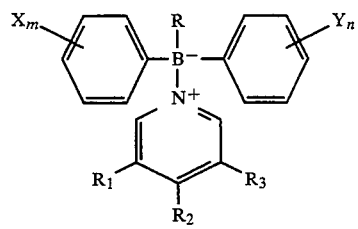

and their use for the prevention, control or amelioration of diseases caused by phytopathogenic fungi. Further provided are compositions and methods comprising those compounds for the protection of plants from fungal infestation and disease.

12 Claims, No Drawings

DIARYL(PYRIDINIO AND ISOQUINOLINIO) BORON FUNGICIDAL AGENTS

BACKGROUND OF THE INVENTION

Phytopathogenic fungi are the causal agents for many diseases that infect and destroy crops. In particular, the diseases apple scab, grape downy mildew, tomato early blight and grape and pepper botrytis are especially devastating.

The leaves and fruit of apple trees are susceptible to attack by a fungus, *Venturia inaequalis*, resulting in a disease called apple scab. The disease occurs wherever apples are grown, but is most common in the United States and Europe. Uncontrolled, apple scab results in deformed, low quality fruit.

Tomatoes are also susceptible to diseases caused by fungi. For example, the foliage, stem and fruit of the tomato plant may be attacked by a fungus, *Alternaria solani*, resulting in a disease called tomato early blight. Tomato early blight is particularly destructive in regions with wet or humid climates. Uncontrolled, tomato early blight causes the defoliation of the tomato plant, resulting in reduced fruit number and size.

Grapes and peppers are susceptible to attack by the fungus, *Botrytis cinerea*, causing grape botrytis and pepper botrytis, respectively. Grape botrytis, for example, is an especially destructive disease that destroys the cell walls of the fruit, resulting in bunch rot. Grape botrytis may occur in any grape vineyard, but is most prevalent in Europe.

In spite of the commercial fungicides available today, diseases caused by fungi still abound. Accordingly, there is ongoing research to create new and more effective fungicides for controlling or preventing diseases caused by phytopathogenic fungi.

It is therefore an object of the present invention to provide compounds which are highly effective for controlling or preventing phytopathogenic fungal infestations in agronomic crops, both growing and harvested.

It is also an object of the present invention to provide a method for the prevention, control or amelioration of a disease caused by a phytopathogenic fungus.

These and other objects of the present invention will become more apparent from the detailed description thereof set forth below.

SUMMARY OF THE INVENTION

The present invention describes certain diaryl(pyridinio and isoquinolinio)boron compounds which are useful as fungicidal agents.

The present invention also includes a method for the protection of a plant, plant seed or tuber from fungal infestation and disease which comprises applying to the plant, plant seed or tuber, or to the medium or water in which it is growing, a fungicidally effective amount of a compound having the structural formula

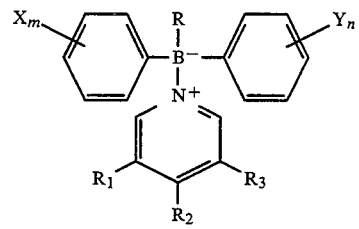

wherein
X and Y are each independently hydrogen, halogen, $C_1$-$C_8$ alkyl, $C_1$-$C_8$ haloalkyl, $C_1$-$C_8$ alkoxy or $C_1$-$C_8$ haloalkoxy;
m and n are each independently an integer of 0, 1, 2 or 3;
R is $C_1$-$C_8$ alkyl, $C_1$-$C_8$ alkoxy, halogen or hydroxy;
$R_1$, $R_2$ and $R_3$ are each independently hydrogen, $C_1$-$C_8$ alkyl, $C_1$-$C_8$ haloalkyl, $C_1$-$C_8$ alkoxy, $C_1$-$C_8$ haloalkoxy, halogen, cyano, nitro, $C(O)R_4$, $NR_5R_6$ or phenyl optionally substituted with one to three halogen, $C_1$-$C_4$ alkyl, $C_1$-$C_4$ haloalkyl, $C_1$-$C_4$ alkoxy, $C_1$-$C_4$ haloalkoxy or $NR_5R_6$ groups, and when taken together, $R_2$ and $R_3$ may form a ring in which $R_2R_3$ is represented by the structure: —$(CH_2)_p$— or

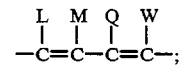

$R_4$, $R_5$ and $R_6$ are each independently hydrogen or $C_1$-$C_4$ alkyl;
p is an integer of 3 or 4; and
L, M, Q and W are each independently hydrogen, halogen, $C_1$-$C_4$ alkyl, $C_1$-$C_4$ haloalkyl, $C_1$-$C_4$ alkoxy, $C_1$-$C_4$ haloalkoxy or nitro.

This invention also relates to compositions and methods for the prevention, control or amelioration of diseases caused by phytopathogenic fungi.

DETAILED DESCRIPTION OF THE INVENTION

Phytopathogenic fungi are the causal agents for many diseases that infect and destroy agronomic crops, both growing and harvested. In the United States alone, agronomic crops must compete with about 18,000 species of fungi. Especially devasting are diseases such as apple scab, grape downy mildew, tomato early blight, grape or pepper botrytis and the like. Accordingly, there is ongoing research to create new and more effective fungicides for preventing or controlling the vast array of fungal infestations of crops.

Advantageously, the present invention provides a method for the prevention, control or amelioration of a disease caused by a phytopathogenic fungus by contacting said fungus with a fungicidally effective amount of a diaryl(pyridinio or isoquinolinio)boron compound.

The present invention also provides a method for the protection of a plant, plant seed or tuber from fungal infestation and disease by applying to the plant, plant seed or tuber, or to the medium or water in which it is growing, a fungicidally effective amount of a diaryl(pyridinio or isoquinolinio)boron compound.

The term "medium" used herein is defined as any environment, including but not limited to artificial nutrients or soil, in which a plant can be kept, live or thrive.

The novel fungicidal diaryl(pyridinio and isoquinolinio)boron compounds of the present invention have the following structural formula I:

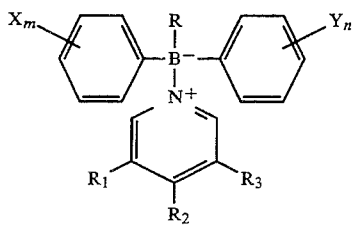

wherein
X and Y are each independently hydrogen, halogen, $C_1$-$C_8$ alkyl, $C_1$-$C_8$ haloalkyl, $C_1$-$C_8$ alkoxy or $C_1$-$C_8$ haloalkoxy;

m and n are each independently an integer of 0, 1, 2 or 3;

R is $C_1$-$C_8$ alkyl, $C_1$-$C_8$ alkoxy, halogen or hydroxy;

$R_1$, $R_2$ and $R_3$ are each independently hydrogen, $C_1$-$C_8$ alkyl, $C_1$-$C_8$ haloalkyl, $C_1$-$C_8$ alkoxy, $C_1$-$C_8$ haloalkoxy, halogen, cyano, nitro, $C(O)R_4$, $NR_5R_6$ or phenyl optionally substituted with one to three halogen, $C_1$-$C_4$ alkyl, $C_1$-$C_4$ haloalkyl, $C_1$-$C_4$ alkoxy, $C_1$-$C_4$ haloalkoxy or $NR_5R_6$ groups, and when taken together, $R_2$ and $R_3$ may form a ring in which $R_2R_3$ is represented by the structure: —$(CH_2)_p$— or

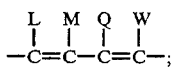

$R_4$, $R_5$ and $R_6$ are each independently hydrogen or $C_1$-$C_4$ alkyl;

p is an integer of 3 or 4; and

L, M, Q and W are each independently hydrogen, halogen, $C_1$-$C_4$ alkyl, $C_1$-$C_4$ haloalkyl, $C_1$-$C_4$ alkoxy, $C_1$-$C_4$ haloalkoxy or nitro; provided that when each of $R_1$, $R_2$ and $R_3$ is hydrogen or t-butyl then R must be other than halogen; and further provided that when X, Y, $R_1$, $R_2$ and $R_3$ are each hydrogen, then R must be hydroxy.

The term halogen used herein included fluorine, chlorine, bromine and iodine.

Compounds of formula I which are preferred in the methods and compositions of the present invention are those wherein X and Y are each independently hydrogen, halogen, $C_1$-$C_8$ alkyl or $C_1$-$C_8$ haloalkyl;

m and n are each independently an integer of 0, 1 or 2;

R is $C_1$-$C_8$ alkyl, $C_1$-$C_8$ alkoxy, halogen or hydroxy;

$R_1$, $R_2$ and $R_3$ are each independently hydrogen, $C_1$-$C_8$ alkyl, $C_1$-$C_8$ haloalkyl, halogen, cyano, $C(O)R_4$ or phenyl, and when taken together, $R_2$ and $R_3$ may form a ring in which $R_2R_3$ is represented by the structure: —$(CH_2)_4$— or

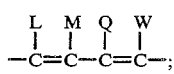

$R_4$ is $C_1$-$C_4$ alkyl; and

L, M, Q and W are each independently hydrogen, halogen, $C_1$-$C_4$ alkyl, $C_1$-$C_4$ haloalkyl or nitro.

More preferred formula I fungicidal agents of the present invention are those wherein X and Y are each independently hydrogen, halogen or $C_1$-$C_8$ alkyl;

m and n are each independently an integer of 0, 1 or 2;

R is $C_1$-$C_8$ alkyl;

$R_1$, $R_2$ and $R_3$ are each independently hydrogen, $C_1$-$C_8$ alkyl, halogen, cyano, $C(O)R_4$ or phenyl, and when taken together, $R_2$ and $R_3$ may form a ring in which $R_2R_3$ is represented by the structure: —$(CH_2)_4$— or —CL=CH—CH=CH—;

$R_4$ is $C_1$-$C_4$ alkyl; and

L is hydrogen or nitro.

Diaryl(pyridinio and isoquinolinio)boron compounds of the present invention which are particularly effective fungicidal agents include (5,6,7,8-tetrahydroisoquinolinio)methyldiphenylboron; (isoquinolinio)methyldiphenylboron; bis(p-fluorophenyl)(isoquinolinio)methylboron; (4-isopropylpyridinio)methyldiphenylboron; methyl(3-methylpyridinio)diphenylboron; (3-butylpyridinio)methyldiphenylboron; and (3-ethyl-4-methylpyridinio)methyldiphenylboron, among others.

The diaryl(pyridinio and isoquinolinio)boron compounds of the present invention are useful in the prevention, control or amelioration of diseases such as apple scab, grape downy mildew, tomato early blight and grape or pepper botrytis. Such diseases are caused by the phytopathogenic fungi *Venturia inaequalis*, *Plasmopara viticola*, *Alternaria solani* and *Botrytis cinerea*, respectively.

Diaryl(pyridinio and isoquinolinio)boron compounds of formula I wherein R is $C_1$-$C_8$ alkyl may be prepared by reacting a diarylborinic acid ethanolamine ester of formula II with an alkyl magnesium halide of formula III to form an intermediate of formula IV and reacting said formula IV intermediate with a pyridine or isoquinoline of formula V as shown in Flow Diagram I.

FLOW DIAGRAM I

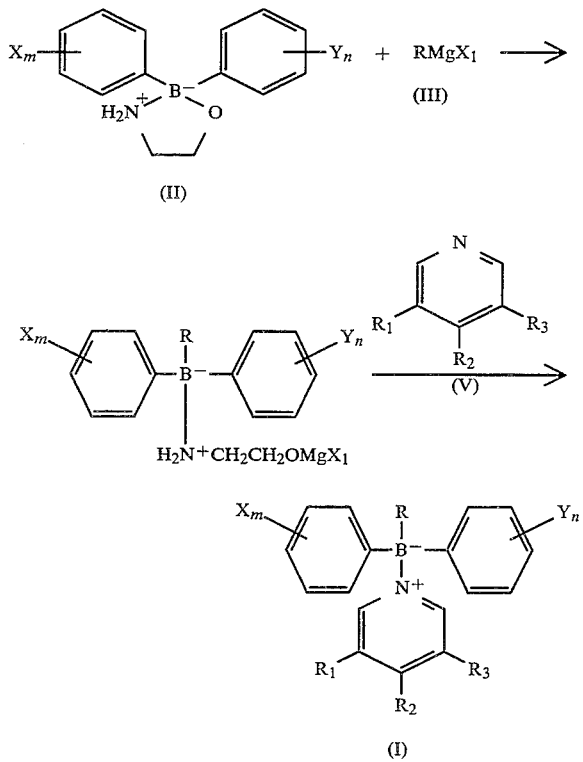

wherein X, Y, m, n, $R_1$, $R_2$ and $R_3$ are as described hereinabove for formula I;
R is $C_1-C_8$ alkyl; and
$X_1$ is chlorine, bromine or iodine.

Fungicidal diaryl(pyridinio and isoquinolinio)boron compounds of formula I wherein R is $C_1-C_8$ alkoxy, halogen or hydroxy may be prepared by reacting a diarylboron compound of formula VI with a pyridine or isoquinoline of formula V as shown in Flow Diagram II.

FLOW DIAGRAM II

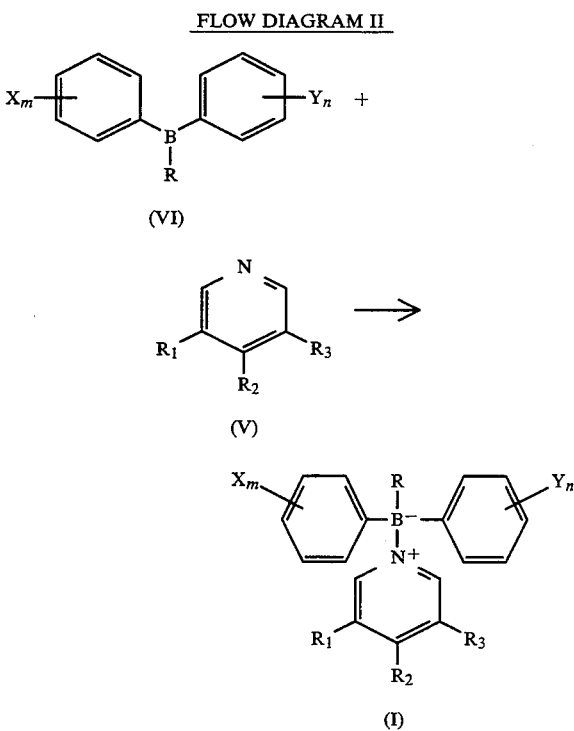

wherein X, Y, m, n, $R_1$, $R_2$ and $R_3$ are as described hereinabove for formula I; and
R is $C_1-C_8$ alkoxy, halogen or hydroxy.

The formula I compounds of the present invention are especially useful for controlling or preventing the growth of phytopathogenic fungi such as *Venturia inaequalis*, *Plasmopara viticola*, *Alternaria solani* and *Botrytis cinerea*. Therefore, harmful diseases such as apple scab, grape downy mildew, tomato early blight and grape and pepper botrytis may be prevented or controlled.

Fungi controlled or ameliorated by the formula I compounds of this invention include Ascomycetes such as *Venturia inaequalis*, *Erysiphe graminis* f.sp. *tritici*, *Leptosphaeria nodorum*, *Alternaria solani*, *Cercospora beticola*, *Botrytis cinerea*, *Pseudocercosporella herpotrichoides*, *Fusarium oxysporum* and *Pyricularia grisea* f.sp. *oryzae*; Basidiomycete such as *Thanatephorus cucumeris* and *Puccinia recondita*; and Oomycete such as *Plasmopara viticola* and *Pythium ultimum*. Advantageously, it has been found that the compounds of the present invention are especially effective against *Venturia inaequalis*, *Plasmopara viticola*, *Alternaria solani* and *Botrytis cinerea*.

The compounds of the present invention are also useful for the protection of growing or harvested plants from the damage caused by photopathogenic fungal disease when applied to said plants at a fungicidally effective rate. The effective rate will vary depending upon factors such as the virulence of the target fungus, the environment of the treatment and other ambient conditions. In practice, generally about 20 ppm to 1,000 ppm, preferably about 50 ppm to 500 ppm of a formula I compound may be dispersed in a liquid or solid carrier and applied to the plant, seed or tuber, or to the medium or water in which the plant, seed or tuber is growing.

The compounds of the invention may be formulated as concentrated solutions, emulsifiable concentrates, flowable concentrates, microemulsions and the like. Said compounds may also be formulated as dry compacted granules, granular compositions, dusts, dust concentrates, suspension concentrates, wettable powders, and the like. Those formulations which lend themselves to seed, tuber, medium, water and/or foliage applications to provide the requisite plant protection are suitable. Such formulations include the compounds of the invention admixed with an inert solid or liquid carrier.

It is contemplated that the compounds of the invention may be used in conjunction with, or in combination with, a pesticidally effective amount of one or more other pesticides, including but not limited to, anilazine, benalaxyl, benomyl, bitertanol, bordeaux mixture, carbendazim, carboxin, captafol, captan, chlorothalonil, cyproconazole, dichloran, diethofencarb, diniconazole, dithianon, dodine, edifenphos, fenarimol, fenbuconazole, fenfuram, fenpropidin, fenpropimorph, fentin hydroxide, ferbam, flusilazole, flusulfamide, flutriafol, folpet, fosetyl, fuberidazole, guazatine, hexaconazole, imazalil, iprobenfos, iprodione, mancozeb, maneb, metalaxyl, metiram, myclobutanil, nuarimol, ofurace, oxadixyl, oxycarboxin, penconazole, probenazole, prochloraz, propiconazole, pyrazophos, tebuconazole, thiabendazole, thiophanate, thiphanate-methyl, triadimefon, triadimenol, triarimol, tricyclazole, tridemorph, triflumizole, triforine, vinclozolin, and/or zineb.

Where compositions of the invention are to be employed in combination treatments with other pesticidal agents, the composition may be applied concurrently as an admixture of the components as described above, or may be applied sequentially.

In order to facilitate a further understanding of the invention, the following examples are presented primarily for the purpose of illustrating more specific details thereof. The invention should not be deemed limited thereby except as defined in the claims.

EXAMPLE 1

Preparation of (5,6,7,8-Tetrahydroisoquinolinio)methyldiphenylboron

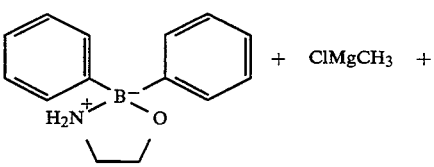

-continued

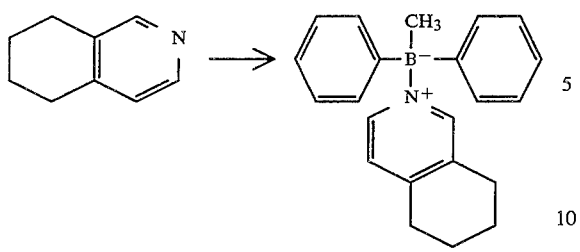

A solution of methyl magnesium chloride in methylene chloride (5.11 mL of a 3 molar solution) is added dropwise to a solution of diphenylborinic acid ethanolamine ester (1.15 g, 5.11 mmol) in tetrahydrofuran. The reaction mixture is stirred for three hours at room temperature, treated with 5,6,7,8-tetrahydroisoquinoline (2.04 g, 15.33 mmol), stirred overnight at room temperature, treated with 5% hydrochloric acid and diluted with ether. The phases are separated and the organic phase is washed sequentially with 5% hydrochloric acid and water, dried over $Na_2SO_4$ and concentrated in vacuo to obtain the title product as a white solid (1.41 g, mp 120°–121° C.).

Using essentially the same procedure, and employing methyl magnesium chloride or methyl magnesium bromide and the appropriately substituted pyridine or isoquinoline, the following compounds are obtained:

| X | Y | $R_1$ | $R_2$ | $R_3$ | mp° C. |
|---|---|---|---|---|---|
| F | F | H | —CH=CH—CH=CH— | | 146–150 |
| F | F | Br | —CH=CH—CH=CH— | | oil |
| F | F | H | —C=CH—CH=CH—<br>w<br>$NO_2$ | | oil |
| H | H | H | H | $(CH_2)_3CH_3$ | oil |
| H | H | H | $CH(CH_3)_2$ | H | 155–156 |
| H | H | H | H | $CH_3$ | 85–86 |
| H | H | H | $CH_3$ | $CH_2CH_3$ | oil |
| H | H | H | —CH=CH—CH=CH— | | 130–132 |
| H | H | H | CN | H | 85 |
| H | H | H | $C_6H_5$ | H | 145–146 |
| H | H | Br | H | H | 132 |
| H | H | H | $C(O)CH_3$ | H | oil |
| H | H | H | $C(CH_3)_3$ | H | 165–168 |

EXAMPLE 2

Preparation of Chloro(isoquinolinio)di-p-tolylboron

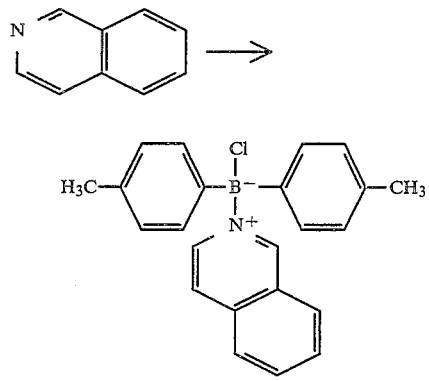

Isoquinoline (0.25 mL, 2.13 mmol) is added to a solution of chloro-di-p-tolylborane (0.5 g, 2.19 mmol) in ether. The reaction mixture is stirred overnight at room temperature and concentrated in vacuo to give the title product as a pale orange oil, 0.7 g, which is identified by $^1$HNMR spectral analysis.

EXAMPLE 3

Preparation of Hydroxy(3-butylpyridinio)diphenylboron

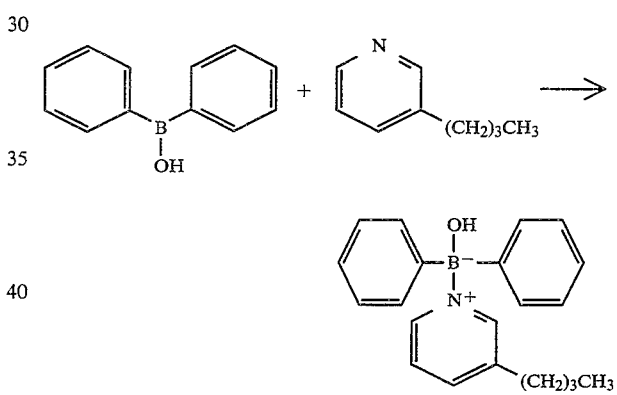

A mixture of diphenylborinic acid (0.5 g, 2.73 mmol) and 3-butylpyridine (0.37 g, 2.74 mmol) in ether is stirred at room temperature for two hours, dried over $Na_2SO_4$ and concentrated in vacuo to give the title product as a pale yellow oil, 0.76 g, which is identified by $^1$H and $^{13}$CNMR spectral analyses.

Using essentially the same procedure, but substituting 4-isopropylpyridine for 3-butylpyridine, hydroxy(4-isopropylpyridinio)diphenylboron is obtained as a pale yellow oil.

EXAMPLE 4

Preparation of Butoxy(4-methylpyridinio)diphenylboron

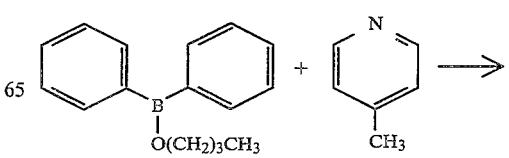

-continued

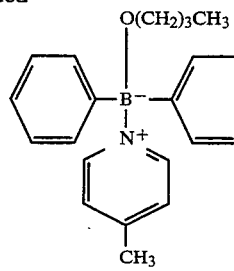

A mixture of butyl diphenylborinate (0.5 g, 2.09 mmol) and 4-picoline (0.206 mL, 2.18 mmol) in ether is stirred for thirty minutes at 0° C. and concentrated in vacuo to obtain the title product as a pale yellow oil, 0.51 g, which is identified by ¹HNMR spectral analysis.

Using essentially the same procedure, and employing the appropriately substituted pyridine, the following compounds are obtained and characterized by ¹HNMR spectral analyses:

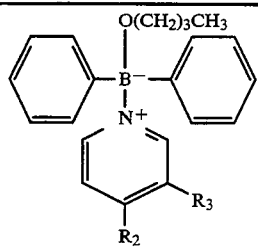

| $R_2$ | $R_3$ | |
|---|---|---|
| H | $CH_3$ | yellow oil |
| $CH(CH_3)_2$ | H | yellow oil |

EXAMPLE 5

Evaluation of in vivo fungitidal activity of test compounds

Test compounds are dissolved or suspended in acetone and diluted with deionized water containing about 0.05% TWEEN 20,, a polyoxyethylene sorbitan monolaurate surfactant manufactured by Atlas Chemical Industries, to give a concentration of 200 ppm.

Host plants are sprayed with the test solution, dried and inoculated with fungi. When disease symptom development is optimal, the plants are rated for disease control according to the rating scale shown below. Each test contains inoculated treated plants, inoculated untreated plants and a reference standard. When more than one test is run, the data are averaged. The data obtained are shown in Table I.

Compounds employed in this in vivo fungicidal evaluation and in the in vitro fungicidal evaluation in the following example are given a compound number and identified by name. Data in Table I are reported by compound number.

| RATING SCALE | |
|---|---|
| Rating | Range % Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| — | no evaluation |

| PHYTOPATHOGENIC FUNGI | | |
|---|---|---|
| Symbol | Disease | Pathogen |
| AS | Apple Scab | Venturia inaequalis |
| GDM | Grape Downy Mildew | Plasmopara viticola |
| PB | Pepper Botrytis | Botrytis cinerea |
| RB | Rice Blast | Pyricularia oryzae |
| SBC | Sugar Beet Cercospora | Cercospora beticola |
| TEB | Tomato Early Blight | Alternaria solani |
| WLR | Wheat Leaf Rust | Puccinia recondita f. sp. tritici |
| WPM | Wheat Powdery Mildew | Erysiphe graminis f. sp. tritici |

| COMPOUNDS EVALUATED AS FUNGICIDAL AGENTS | |
|---|---|
| Compound No. | |
| 1 | (4-Isopropylpyridinio)methyldiphenylboron |
| 2 | Methyl(3-methylpyridinio)diphenylboron |
| 3 | (3-Butylpyridinio)methyldiphenylboron |
| 4 | (5,6,7,8-Tetrahydroisoquinolinio)methyldiphenylboron |
| 5 | (3-Ethyl-4-methylpyridinio)methyldiphenylboron |
| 6 | (Isoquinolinio)methyldiphenylboron |
| 7 | Hydroxy(3-butylpyridinio)diphenylboron |
| 8 | Hydroxy(4-isopropylpyridinio)diphenylboron |
| 9 | Butoxy(4-methylpyridinio)diphenylboron |
| 10 | Butoxy(3-methylpyridinio)diphenylboron |
| 11 | Butoxy(4-isopropylpyridinio)diphenylboron |
| 12 | Chloro(isoquinolinio)di-p-tolylboron |
| 13 | Bis(p-fluorophenyl) (isoquinolinio)methylboron |
| 14 | (4-Bromoisoquinolinio)bis(p-fluorophenyl)-methylboron |
| 15 | Bis(p-fluorophenyl)methyl(5-nitroisoquinolinio)boron |
| 16 | (4-Cyanopyridinio)methyldiphenylboron |
| 17 | (4-Phenylpyridinio)methyldiphenylboron |
| 18 | (3-Bromopyridinio)methyldiphenylboron |
| 19 | (4-Acetylpyridinio)methyldiphenylboron |
| 20 | (4-Tert-butyl-pyridinio)methyldiphenylboron |

TABLE I

| | | In Vivo Fungicidal Evaluations | | | | | | | |
|---|---|---|---|---|---|---|---|---|---|
| Compound No. | Rate (ppm) | AS | GDM | PB | RB | SBC | TEB | WLR | WPM |
| 1 | 200 | 9 | 9 | 7 | 7 | 0 | 7 | 8 | 8 |
| 2 | 200 | 9 | 9 | 0 | 7 | 0 | 0 | 8 | 8 |
| 3 | 200 | 9 | 9 | 6 | 0 | 0 | 8 | 8 | 8 |
| 4 | 200 | 9 | 9 | 9 | 0 | 8 | 6 | 9 | 8 |
| 5 | 200 | 0 | 9 | 0 | 0 | 0 | 8 | 8 | 9 |
| 6 | 200 | 9 | 9 | 0 | 6 | 0 | 0 | 9 | 8 |
| 7 | 200 | 6 | 0 | 0 | 6 | 0 | 0 | 5 | 5 |

TABLE I-continued

| | | In Vivo Fungicidal Evaluations | | | | | | | |
|---|---|---|---|---|---|---|---|---|---|
| Compound No. | Rate (ppm) | AS | GDM | PB | RB | SBC | TEB | WLR | WPM |
| 8 | 200 | 0 | 4 | 0 | 6 | 0 | 0 | 0 | 0 |
| 9 | 200 | 0 | 0 | 6 | 0 | 0 | 0 | 0 | 0 |
| 10 | 200 | 0 | 3 | 6 | 0 | 0 | 0 | 0 | 0 |
| 11 | 200 | 8 | 0 | 4 | 0 | 0 | 0 | 0 | 0 |
| 12 | 200 | 0 | 0 | 0 | 0 | 7 | 0 | 0 | 0 |
| 13 | 200 | 7 | 9 | 9 | 7 | 8 | 8 | 7 | 8 |
| 14 | 200 | 8 | 7 | 9 | 8 | 7 | 0 | 0 | 0 |
| 15 | 200 | 9 | 0 | 9 | 3 | 7 | 4 | 0 | 0 |
| 16 | 200 | 9 | 9 | 8 | 9 | 8 | 8 | — | 0 |
| 17 | 200 | 9 | 9 | 9 | 8 | 8 | 9 | — | 8 |
| 18 | 200 | 0 | 4 | 8 | 5 | 6 | 4 | 0 | 0 |
| 19 | 200 | 9 | 9 | 9 | 8 | 9 | 8 | — | 8 |
| 20 | 200 | 9 | 9 | 9 | 8 | 9 | 8 | — | 7 |

EXAMPLE 6

Evaluation of in vitro fungicidal activity of test compounds

Test compounds are dissolved or suspended in acetone and dispersed into cell well plates containing a suspension of ground fungal mycelia in a nutrient broth. Assay plates are incubated for 3-4 days at 21° C. Growth inhibition is measured visually and is rated using the following scale:

| RATING SCALE | |
|---|---|
| Rating | Range % Control |
| 0 | 0 |
| 1 | 1-29 |
| 3 | 30-59 |
| 5 | 60-89 |
| 7 | 90-99 |
| 9 | 100 |

Untreated controls, solvent blanks and reference standards are included in each test.

Assay fungi include the plant pathogens, *Pythium ultimum* (Pythul); *Rhizoctonia solani* (Rhizso); *Fusarium oxysporum* f. sp. *cucumerinum* (Fusoxc); and *Pseudocercosporella herpotrichoides* (Psdche).

When more than one test is run, the data are averaged. The data obtained are shown in Table II. The compounds evaluated are reported by compound number given in Example 5.

TABLE II

| | | In Vitro Fungicidal Evaluations | | | |
|---|---|---|---|---|---|
| Compound No. | Rate (ppm) | FUSOXC | PSDCHE | PHTHUL | RHIZSO |
| 1 | 25 | 9 | 9 | 7 | 9 |
| 2 | 25 | 9 | 9 | 9 | 9 |
| 3 | 25 | 9 | 9 | 9 | 9 |
| 4 | 25 | 9 | 9 | 7 | 9 |
| 5 | 25 | 9 | 9 | 9 | 9 |
| 6 | 25 | 9 | 9 | 9 | 7 |
| 7 | 25 | 9 | 0 | 9 | 9 |
| 8 | 25 | 9 | 0 | 9 | 7 |
| 9 | 25 | 9 | 0 | 9 | 0 |
| 10 | 25 | 9 | 7 | 9 | 9 |
| 11 | 25 | 9 | 7 | 9 | 9 |
| 12 | 25 | 7 | 5 | 7 | 7 |
| 13 | 25 | 9 | 9 | 9 | 9 |
| 14 | 25 | 9 | 9 | 9 | 9 |
| 15 | 25 | 9 | 9 | 9 | 9 |
| 16 | 25 | 7 | 9 | 7 | 7 |
| 17 | 25 | 7 | 7 | 0 | 5 |
| 18 | 25 | 7 | 9 | 7 | 7 |

TABLE II-continued

| | | In Vitro Fungicidal Evaluations | | | |
|---|---|---|---|---|---|
| Compound No. | Rate (ppm) | FUSOXC | PSDCHE | PHTHUL | RHIZSO |
| 19 | 25 | 7 | 9 | 7 | 7 |
| 20 | 25 | 7 | 7 | 7 | 7 |

I claim:

1. A method for the control or amelioration of a disease caused by a phytopathogenic fungus which comprises contacting said fungus with a fungicidally effective amount of a compound having the structural formula

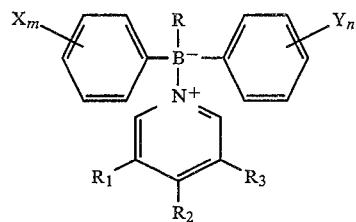

wherein
X and Y are each independently hydrogen, halogen, $C_1$-$C_8$ alkyl, $C_1$-$C_8$ haloalkyl, $C_1$-$C_8$ alkoxy or $C_1$-$C_8$ haloalkoxy;
m and n are each independently an integer of 0, 1, 2 or 3;
R is $C_1$-$C_8$ alkyl, $C_1$-$C_8$ alkoxy, halogen or hydroxy;
$R_1$, $R_2$ and $R_3$ are each independently hydrogen, $C_1$-$C_8$ alkyl, $C_1$-$C_8$ haloalkyl, $C_1$-$C_8$ alkoxy, $C_1$14 $C_8$ haloalkoxy, halogen, cyano, nitro, C(O)$R_4$, $NR_5R_6$ or phenyl optionally substituted with one to three halogen, $C_1$-$C_4$ alkyl, $C_1$-$C_4$ haloalkyl, $C_1$14 $C_4$ alkoxy, $C_1$-$C_4$ haloalkoxy or $NR_5R_6$ groups, and when taken together, $R_2$ and $R_3$ may form a ring in which $R_2R_3$ is represented by the structure:
—$(CH_2)_p$— or

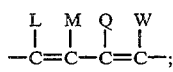

$R_4$, $R_5$ and $R_6$ are each independently hydrogen or $C_1$-$C_4$ alkyl;
p is an integer of 3 or 4; and L, M, Q and W are each independently hydrogen, halogen, $C_1$-$C_4$ alkyl, $C_1$-$C_4$ haloalkyl, $C_1$-$C_4$ alkoxy, $C_1$-$C_4$ haloalkoxy or nitro.

2. The method according to claim 1 wherein

X and Y are each independently hydrogen, halogen, $C_1$-$C_8$ alkyl or $C_1$-$C_8$ haloalkyl;

m and n are each independently an integer of 0, 1 or 2;

$R_1$, $R_2$ and $R_3$ are each independently hydrogen, $C_1$-$C_8$ alkyl, $C_1$-$C_8$ haloalkyl, halogen, cyano, $C(O)R_4$ or phenyl, and when taken together, $R_2$ and $R_3$ may form a ring in which $R_2R_3$ is represented by the structure: —$(CH_2)_4$— or

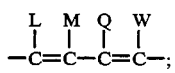

$R_4$ is $C_1$-$C_4$ alkyl; and

L, M, Q and W are each independently hydrogen, halogen, $C_1$-$C_4$ alkyl, $C_1$-$C_4$ haloalkyl or nitro.

3. The method according to claim 2 wherein

X and Y are each independently hydrogen, halogen or $C_1$-$C_8$ alkyl;

R is $C_1$-$C_8$ alkyl;

$R_1$, $R_2$ and $R_3$ are each independently hydrogen, $C_1$-$C_8$ alkyl, halogen, cyano, $C(O)R_4$ or phenyl, and when taken together, $R_2$ and $R_3$ may form a ring in which $R_2R_3$ is represented by the structure —$(CH_2)_4$— or —CL=CH—CH=CH—; and L is hydrogen or nitro.

4. The method according to claim 3 wherein the compound is selected from the group consisting of (5,6,7,8-tetrahydroisoquinolinio)methyldiphenylboron; (isoquinolinio)methyldiphenylboron; bis(p-fluorophenyl)(isoquinolinio)methylboron; (4-isopropylpyridinio)methyldiphenylboron; methyl(3-methylpyridinio)diphenylboron; (3-butylpyridinio)methyldiphenylboron; and (3-ethyl-4-methylpyridinio)methyldiphenylboron.

5. The method according to claim 1 wherein the compound is applied at a concentration of about 20 ppm to 1,000 ppm.

6. A method for the protection of a plant, plant seed or tuber from fungal infestation and disease which comprises applying to the plant, plant seed or tuber, or to the medium or water in which it is growing, a fungicidally effective amount of a compound having the structural formula

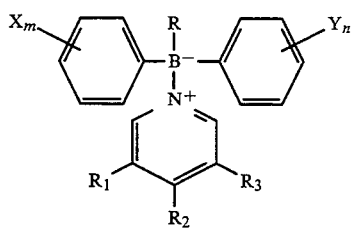

wherein

X and Y are each independently hydrogen, halogen, $C_1$-$C_8$ alkyl, $C_1$-$C_8$ haloalkyl, $C_1$-$C_8$ alkoxy or $C_1$-$C_8$ haloalkoxy;

m and n are each independently an integer of 0, 1, 2 or 3;

R is $C_1$-$C_8$ alkyl, $C_1$-$C_8$ alkoxy, halogen or hydroxy;

$R_1$, $R_2$ and $R_3$ are each independently hydrogen, $C_1$-$C_8$ alkyl, $C_1$-$C_8$ haloalkyl, $C_1$-$C_8$ alkoxy, $C_1$-$C_8$ haloalkoxy, halogen, cyano, nitro, $C(O)R_4$, $NR_5R_6$ or phenyl optionally substituted with one to three halogen, $C_1$-$C_4$ alkyl, $C_1$-$C_4$ haloalkyl, $C_1$-$C_4$ alkoxy, $C_1$-$C_4$ haloalkoxy or $NR_5R_6$ groups, and when taken together, $R_2$ and $R_3$ may form a ring in which $R_2R_3$ is represented by the structure: —$(CH_2)_p$— or

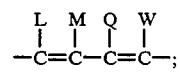

$R_4$, $R_5$ and $R_6$ are each independently hydrogen or $C_1$-$C_4$ alkyl;

p is an integer of 3 or 4; and

L, M, Q and W are each independently hydrogen, halogen, $C_1$-$C_4$ alkyl, $C_1$-$C_4$ haloalkyl, $C_1$-$C_4$ alkoxy, $C_1$-$C_4$ haloalkoxy or nitro.

7. The method according to claim 6 wherein X and Y are each independently hydrogen, halogen, $C_1$-$C_8$ alkyl or $C_1$-$C_8$ haloalkyl;

m and n are each independently an integer of 0, 1 or 2;

$R_1$, $R_2$ and $R_3$ are each independently hydrogen, $C_1$-$C_8$ alkyl, $C_1$-$C_8$ haloalkyl, halogen, cyano, $C(O)R_4$ or phenyl, and when taken together, $R_2$ and $R_3$ may form a ring in which $R_2R_3$ is represented by the structure: —$(CH_2)_4$— or

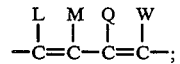

$R_4$ is $C_1$-$C_4$ alkyl; and

L, M, Q and W are each independently hydrogen, halogen, $C_1$-$C_4$ alkyl, $C_1$-$C_4$ haloalkyl or nitro.

8. The method according to claim 7 wherein

X and Y are each independently hydrogen, halogen or $C_1$-$C_8$ alkyl;

R is $C_1$-$C_8$ alkyl;

$R_1$, $R_2$ and $R_3$ are each independently hydrogen, $C_1$-$C_8$ alkyl, halogen, cyano, $C(O)R_4$ or phenyl, and when taken together, $R_2$ and $R_3$ may form a ring in which $R_2R_3$ is represented by the structure: —$(CH_2)_4$ — or —CL=CH—CH=CH—; and L is hydrogen or nitro.

9. The method according to claim 8 wherein the compound is selected from the group consisting of (5,6,7,8-tetrahydroisoquinolinio)methyldiphenylboron; (isoquinolinio)methyldiphenylboron; bis (p-fluorophenyl) (isoquinolinio) methylboron; (4-isopropylpyridinio)methyldiphenylboron; methyl(3-methylpyridinio)diphenylboron; (3-butylpyridinio)methyldiphenylboron; and (3-ethyl-4-methylpyridinio)methyldiphenylboron.

10. A composition for controlling phytopathogenic fungi which comprises an agronomically acceptable inert liquid emulsion or suspension or solid carrier and a fungicidally effective amount of a compound having the structural formula

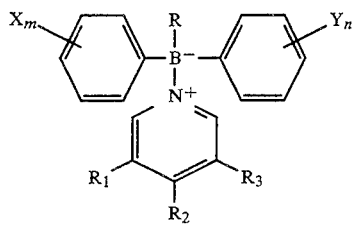

wherein

X and Y are each independently hydrogen, halogen, $C_1$–$C_8$ alkyl, $C_1$–$C_8$ haloalkyl, $C_1$–$C_8$ alkoxy or $C_1$–$C_8$ haloalkoxy;

m and n are each independently an integer of 0, 1, 2 or 3;

R is $C_1$–$C_8$ alkyl, $C_1$–$C_8$ alkoxy, halogen or hydroxy;

$R_1$, $R_2$ and $R_3$ are each independently hydrogen, $C_1$–$C_8$ alkyl, $C_1$–$C_8$ haloalkyl, $C_1$–$C_8$ alkoxy, $C_1$–$C_8$ haloalkoxy, halogen, cyano, nitro, $C(O)R_4$, $NR_5R_6$ or phenyl optionally substituted with one to three halogen, $C_1$–$C_4$ alkyl, $C_1$–$C_4$ haloalkyl, $C_1$–$C_4$ alkoxy, $C_1$–$C_4$ haloalkoxy or $NR_5R_6$ groups, and when taken together, $R_2$ and $R_3$ may form a ring in which $R_2R_3$ is represented by the structure: —$(CH_2)_p$— or

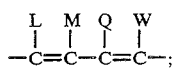

$R_4$, $R_5$ and $R_6$ are each independently hydrogen or $C_1$–$C_4$ alkyl;

p is an integer of 3 or 4; and

L, M, Q and W are each independently hydrogen, halogen, $C_1$–$C_4$ alkyl, $C_1$–$C_4$ haloalkyl, $C_1$–$C_4$ alkoxy, $C_1$–$C_4$ haloalkoxy or nitro.

11. The composition according to claim 10 wherein

X and Y are each independently hydrogen, halogen, $C_1$–$C_8$ alkyl or $C_1$–$C_8$ haloalkyl;

m and n are each independently an integer of 0, 1 or 2;

$R_1$, $R_2$ and $R_3$ are each independently hydrogen, $C_1$–$C_8$ alkyl, $C_1$–$C_8$ haloalkyl, halogen, cyano, $C(O)R_4$ or phenyl, and when taken together, $R_2$ and $R_3$ may form a ring in which $R_2R_3$ is represented by the structure: —$(CH_2)_4$— or

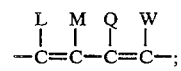

$R_4$ is $C_1$–$C_4$ alkyl; and

L, M, Q and W are each independently hydrogen, halogen, $C_1$–$C_4$ alkyl, $C_1$–$C_4$ haloalkyl or nitro.

12. The composition according to claim 11 wherein

X and Y are each independently hydrogen, halogen or $C_1$–$C_8$ alkyl;

R is $C_1$–$C_8$ alkyl;

$R_1$, $R_2$ and $R_3$ are each independently hydrogen, $C_1$–$C_8$ alkyl, halogen, cyano, $C(O)R_4$ or phenyl, and when taken together, $R_2$ and $R_3$ may form a ring in which $R_2R_3$ is represented by the structure: —$(CH_2)_4$— or —CL=CH—CH=CH—; and L is hydrogen or nitro.

* * * * *